United States Patent [19]

Swarup et al.

[11] Patent Number: 5,413,856
[45] Date of Patent: May 9, 1995

[54] SUSTAINED RELEASE AGRICULTURAL SUBSTRATE COATED WITH A BLEND OF EPDM AND ASPHALT

[75] Inventors: Vijay Swarup, Edmonton; Albert J. Geiger, Fort Saskatchewan, both of Canada; Evelyn N. Drake, Bernardsville, N.J.; Dennis G. Peiffer, Annandale, N.J.; Martin L. Gorbaty, Westfield, N.J.

[73] Assignee: Exxon Research & Engineering Co., Florham Park, N.J.

[21] Appl. No.: 108,098

[22] Filed: Aug. 17, 1993

[51] Int. Cl.⁶ .................... B32B 33/00; A01N 25/00; C05G 5/00
[52] U.S. Cl. .................... 428/334; 71/64.07; 71/64.11; 71/64.13; 428/489; 428/500; 428/402; 428/407
[58] Field of Search .......... 428/220, 483, 489, 334, 428/500, 402, 407; 71/64.02, 64.06, 64.07, 64.11, 64.13; 524/64, 66, 68, 69, 70, 71

[56] References Cited

U.S. PATENT DOCUMENTS

| | | | |
|---|---|---|---|
| 3,276,857 | 10/1966 | Stansbury | 71/64 |
| 4,617,227 | 10/1986 | Weaver | 428/220 |
| 4,738,997 | 4/1988 | Lundberg et al. | 524/68 |
| 4,988,377 | 1/1991 | Manalastas et al. | 71/28 |
| 5,211,985 | 5/1993 | Shirley, Jr. et al. | 71/64.02 X |

Primary Examiner—Paul J. Thibodeau
Assistant Examiner—Stephen Sand
Attorney, Agent, or Firm—Joseph J. Dvorak

[57] ABSTRACT

There is provided a coated agricultural substrate in which the coating comprises a blend of a neutralized sulfonated ionomer and asphalt. Preferably, the coating contains from about 1 to 20 wt. % asphalt and from 99 to 80 wt. % of the neutralized sulfonated ionomer. In a particularly preferred embodiment of the present invention, the coating contains about 7 wt. % asphalt and about 93 wt. % of the neutralized sulfonated ionomer.

6 Claims, 1 Drawing Sheet

SUSTAINED RELEASE AGRICULTURAL SUBSTRATE COATED WITH A BLEND OF EPDM AND ASPHALT

FIELD OF THE INVENTION

The present invention relates to coated agricultural substrates such as fertilizers.

DESCRIPTION OF THE PRIOR ART

Elastomeric sulfonated ionomers, such as sulfonated ethylene propylene diene (EPDM), terpolymers have been shown to be useful coating materials for fertilizers because of their water barrier properties, their elasticity and ability to be applied as thin continuous coatings free of pinholes. In this regard, see, for example, U.S. Pat. No. 4,988,377, which discloses the use of sulfonated elastomers as coating materials for agricultural substrates.

Although elastomeric sulfonated EPDM materials have been successfully used for preparing slow release fertilizers, there remains a need to provide slow release fertilizers that are capable of releasing their nutrients over longer periods of time; for example, up to about six months at temperatures in the range of about 38° C.

SUMMARY OF THE INVENTION

According to the present invention, there is provided a coated agricultural substrate in which the coating comprises a blend of a neutralized sulfonated ionomer and asphalt. Preferably, the coating contains from about 1 to 20 wt. % asphalt and from 99 to 80 wt. % of the neutralized sulfonated ionomer. In a particularly preferred embodiment of the present invention, the coating contains about 7 wt. % asphalt and about 93 wt. % of the neutralized sulfonated ionomer.

DETAILED DESCRIPTION OF THE INVENTION

Figure 1:
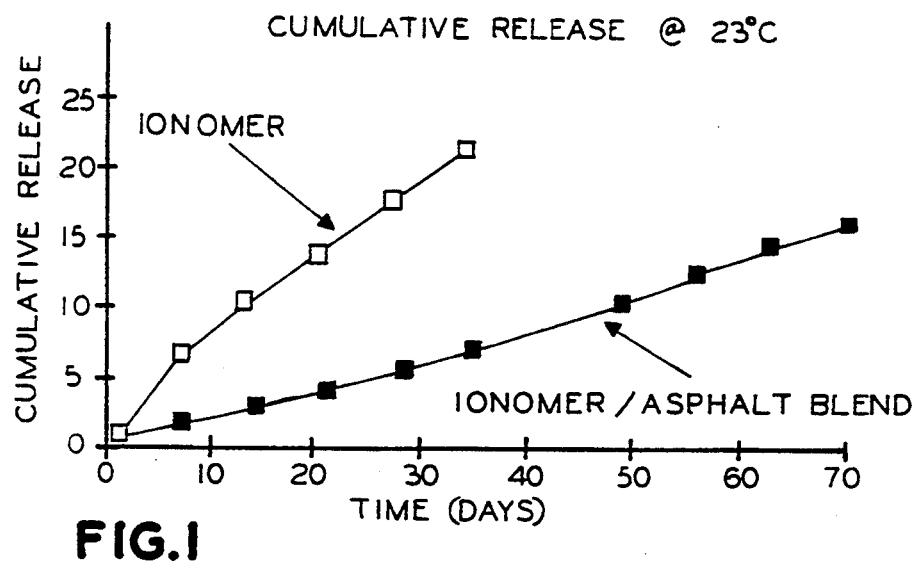
FIG. 1 is a graph comparing the release profile at 23° C. for a urea encapsulated with ionomer to a urea encapsulated with an ionomer/asphalt blend.

The composite structure of the present invention includes an agricultural substrate such as a fertilizer, plant hormone, pesticide, fungicide and mixtures thereof that are made available to plants for the purpose of stimulating the plant growth and protecting the plant against various insects and diseases so as to increase both the yield and improve the quality of the plant. The composite of the present invention also includes a coating on the agricultural substrate which will provide for a sustained release of the agricultural substrate over a period of time under conditions of use, thereby achieving more efficient use of the agricultural substrate, while minimizing the number of applications of the substrate that might otherwise be necessary.

In the composite of the present invention, the coating is a blend of a neutralized sulfonated ionomer and asphalt. Preferably, the ionomer is a neutralized sulfonated EPDM polymer containing from about 4 to about 200 meq. of pendant sulfonate groups per 100 grams of polymer and, more preferably, from about 10 to about 100 meq. of pendant sulfonate groups. These pendant sulfonate groups are neutralized with metal ions from Groups IA, IIA and IIB of the Periodic Table of the Elements, such as zinc, sodium, potassium and the like and ammonium counterions. The Periodic Table referred to is that shown on the inside cover of Lange's Handbook of Chemistry, 11th Edition, McGraw Hill Book Company, 1973. Neutralization is achieved, for example, by contacting the acid form of the polymer with an appropriate metal hydroxide, metal acetate, metal oxide or ammonium hydroxide.

The degree of neutralization of the sulfonate groups may vary widely, but generally will be greater than about 2 mole percent up to about 100 mole percent. It is particularly preferred, however, that the degree of neutralization be substantially complete; that is, with no free acid present.

The asphalt used in the practice of the present invention has a penetration number as determined by ASTM Test Method D-5 of from about 20 to 300 measured at 25° C. and, more preferably, from about 100 to 250 at 25° C. Optionally, the asphalt may be sulfonated and neutralized, as is the polymeric material, although it is not necessary to sulfonate and neutralize the asphalt. In those instances in which the asphalt is, in fact, sulfonated and neutralized, the sulfonation and neutralization can be achieved by techniques well known in the art, such as that disclosed in U.S. Pat. No. 4,514,308. In general, when using a sulfonated asphalt, the asphalt will contain from about 1 to about 100 meq. of sulfonate groups per 100 grams of asphalt and, more preferably, from about 5 to about 40 meq. of sulfonate groups. These pendant sulfonate groups may be neutralized with the same neutralizing agents as are set forth above in connection with the sulfonated polymer. The degree of neutralization of the sulfonated asphalt groups may vary widely, but generally will be greater than about 80 mole percent up to about 100 mole percent.

The ratio of neutralized sulfonated ionomer to asphalt in the composition of the present invention will generally be in the range of from about 99:1 to about 80:20 and, preferably, in the range of from about 97:3 to about 90:10.

The coatings of the present invention are formed by applying an organic solution of both the polymer and asphalt to the substrate at ambient temperatures or at temperatures in the range of about 10° C. to about 50° C. by either dip-coating, spraying or with the use of other techniques for thin spreading, such as brushing. The organic solvent system is then permitted to evaporate with or without the aid of forced drying gas, such as air or nitrogen. The drying gas temperature can be from ambient temperature up to the boiling point of the organic solvent system. Preferably, the temperature of the drying gas is between about 20° C. and about 100° C. The most preferred temperature for the drying gas should be about 50° C. for fast evaporation of the organic solvent system. After drying, the thickness of the applied coating should be about 1 micrometer to about 100 micrometers or from 1 to 4 wt. % based on the weight of the composite. Most preferred, the coating thickness should be about 2 to about 20 micrometers for both performance and economic reasons.

To control the thickness of the applied coating, the solution concentration of the polymer asphalt blend applied is between 1.0 wt. % to 5 wt. %. Most preferably, the concentration should be about 2.5 wt. %.

Normally, the solvent used to form the organic solution will be a solvent such as toluene, xylene, hexane, preferably in combination with a polar solvent such as aliphatic alcohols having from 1 to 10 carbon atoms.

The following examples will demonstrate the performance of the polymer asphalt coating of the present invention.

COMPARATIVE EXAMPLE 1

A 1.25 wt % solution of zinc sulfonated EPDM was made in a 97/3 toluene-methanol mixture. The solution was sprayed on urea in a fluid bed (bed temperature was 50° C.). A 3 wt % coating was applied to the urea.

In order to measure the barrier properties of the coated urea, the following test was conducted: 15 grams of coated substrate were placed in a weighed 250 milliliter flask. 75 grams of distilled water were added and the mixture was incubated at the selected temperature. At prescribed weekly time intervals, the water was decanted from the sample into a weighed aluminum contained and placed in a 98° oven to dry. After drying and cooling, the aluminum container was weighed and the gain in weight represents the amount of substrate released. To the remaining coated material, 75 grams of distilled water were added and the incubation, decantation, etc. was repeated. Repetition of this procedure produced additional data points. The results of these tests are set forth in FIGS. 1 and 2.

EXAMPLE 1

A solution consisting of zinc sulfonated EPDM and asphalt in the weight ratio of 92.5 to 7.5 was prepared by first dissolving the sulfonated EPDM in a toluene-methanol mixture (97/3) and then adding the asphalt to the mixture and allowing the solution to stir for one hour. The resulting solution was then sprayed on urea in a fluid bed in order to obtain a 3 wt % coating. Release rates were measured as described in Comparative Example 1. The results are shown in FIG. 1.

COMPARATIVE EXAMPLE 2

Figure 2:
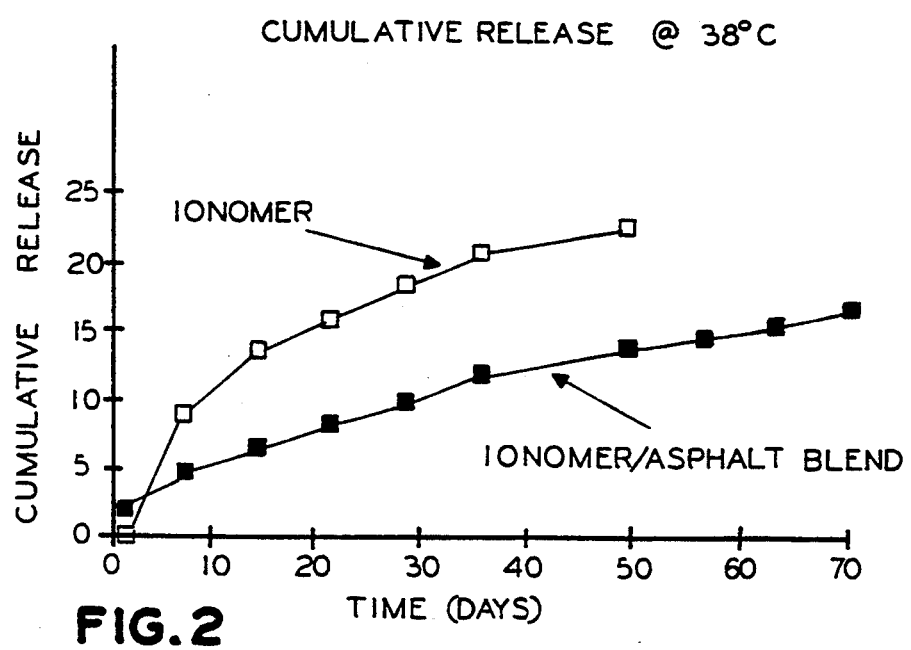
FIG. 2 shows the release profile at 38° C. for urea coated with an ionomer and urea coated with an ionomer/asphalt blend in which the coatings in each case have been crosslinked.

A 3.2 wt % coating of zinc neutralized sulfonated EPDM was applied to urea as described in Comparative Example 1. 300 g of this material was placed in a spinning dish. A solution was prepared by adding 0.90 g $S_2Cl_2$. The solution was sprayed, using a syringe onto the coated urea in the spinning dish. The material was then tested for release as described in Comparative Example 1. The results are shown in FIG. 2.

EXAMPLE 2

A 3.0 wt % coating of a blend of 92.5 zinc sulfonated EPDM and AC-10 asphalt was prepared as described in Example 1. 300g of this material was placed in a spinning dish. A solution was prepared by adding 0.90 g $S_2Cl_2$. The solution was sprayed using a syringe onto the coated urea in the spinning dish. The material was then tested as described in Comparative Example 1. The results are shown in FIG. 2.

From the foregoing, it can be readily appreciated that materials having asphalt ionomer coatings of the present invention are particularly suitable because of their long-term release properties.

What is claimed is:

1. A composite comprising:
   (a) an agricultural substrate selected from the group consisting of fertilizers, pesticides, fungicides, plant hormones and mixtures thereof, and
   (b) a coating on the surface of the agricultural substrate, the coating being a blend of a neutralized sulfonated ethylene-propylene diene terpolymer and an asphalt, the ratio neutralized of sulfonated ethylene-propylene diene terpolymer to asphalt being in the range of about 99:1 to 80:20, the coating being in the range of from 1 wt % to 4 wt % based on the weight of the composite.

2. The composite of claim 1 wherein the ratio of neutralized sulfonated ethylene-propylene diene terpolymer to asphalt is in the range of 97:3 to about 90:10.

3. The composite of claim 1 wherein the asphalt is sulfonated and neutralized.

4. A composite comprising:
   (a) an agricultural substrate selected from the group consisting of fertilizers, pesticides, fungicides, plant hormones and mixtures thereof, and
   (b) a coating on the surface of the substrate, the coating consisting essentially of a blend of a neutralized sulfonated ethylene-propylene diene terpolymer and an asphalt having a penetration number of 20 to 300 as determined by ASTM test method D5, the ratio of neutralized sulfonated ethylene-propylene diene terpolymer and asphalt being in the range of 99:1 to 80:20 and the thickness of the coating being in the range of about 1 to about 100 micrometers.

5. The composite of claim 4 wherein the substrate is a fertilizer and the ratio of neutralized sulfonated ethylene-propylene diene terpolymer to asphalt is 97:3.

6. The composite of claim 5 wherein the asphalt is sulfonated and neutralized.

* * * * *